(12) United States Patent
Shinohara et al.

(10) Patent No.: US 8,327,581 B2
(45) Date of Patent: Dec. 11, 2012

(54) METHOD FOR PRODUCING BIOMINERAL-CONTAINING SUBSTANCE AND ORGANIC HYDROPONICS METHOD

(75) Inventors: Makoto Shinohara, Chita-gun (JP); Yoichi Uehara, Chita-gun (JP); Masato Kouno, Chita-gun (JP); Hirofumi Iwakiri, Chita-gun (JP)

(73) Assignee: Makoto Shinohara, Tsu-shi, Mie (JP)

( * ) Notice: Subject to any disclaimer, the term of this patent is extended or adjusted under 35 U.S.C. 154(b) by 634 days.

(21) Appl. No.: 12/312,569

(22) PCT Filed: Dec. 4, 2006

(86) PCT No.: PCT/JP2006/324146
§ 371 (c)(1),
(2), (4) Date: May 15, 2009

(87) PCT Pub. No.: WO2008/068829
PCT Pub. Date: Jun. 12, 2008

(65) Prior Publication Data
US 2010/0000152 A1    Jan. 7, 2010

(51) Int. Cl.
*A01G 31/00* (2006.01)
(52) U.S. Cl. ........................ 47/62 N; 47/62 R
(58) Field of Classification Search .......... 47/59 R, 47/59 S, 62 R, 62 N, 58.1 R; 435/170, 431; 405/129.65, 129.95
See application file for complete search history.

(56) References Cited

U.S. PATENT DOCUMENTS

| | | | |
|---|---|---|---|
| 3,250,606 A * | 5/1966 | Murray | 71/1 |
| 5,656,059 A * | 8/1997 | Monster et al. | 71/7 |
| 7,350,331 B1 * | 4/2008 | Gontier et al. | 1/1 |
| 2005/0054030 A1 * | 3/2005 | Schnoor et al. | 435/41 |
| 2005/0141966 A1 * | 6/2005 | Greene | 405/129.65 |
| 2011/0126457 A1 * | 6/2011 | Shinohara | 47/59 S |

FOREIGN PATENT DOCUMENTS

| | | |
|---|---|---|
| JP | 06-125668 A | 5/1994 |
| JP | 06-178995 A | 6/1994 |
| JP | 7-177830 A | 7/1995 |

(Continued)

OTHER PUBLICATIONS

Makoto Shinohara et al, "Yukibutsu o Renzoku Mukika suru Biseibutsu Seitaikei ni yoru Yoeki Saibai Tsuchi to Biseibutsu", vol. 60, No. 22, p. 122 (Oct. 2006).

(Continued)

*Primary Examiner* — T. Nguyen
(74) *Attorney, Agent, or Firm* — Holtz Holtz Goodman & Chick PC (57) ABSTRACT

The present invention aims at providing a method for producing a nutrient solution for plant culture utilizing an organic material and providing a method of hydroponic culture in which a plant can be cultured while directly adding the organic material to the nutrient solution. The present invention provides a method for producing a biomineral-containing substance comprising establishing a microbial ecosystem necessary for stable mineralization of organic material by adding the organic material to water gradually or at one time and fermenting the resulting mixture and a method of hydroponic culture comprising utilizing the biomineral-containing substance obtained according to the method as at least a part of the nutrient solution and culturing the plant while directly adding the organic material to the nutrient solution.

16 Claims, 8 Drawing Sheets

FOREIGN PATENT DOCUMENTS

| | | |
|---|---|---|
| JP | 10-245290 A | 9/1998 |
| JP | 10-338583 A | 12/1998 |
| JP | 2000-264765 A | 9/2000 |
| JP | 2001-010885 A | 1/2001 |
| JP | 2002-137979 A | 5/2002 |
| JP | 2003-094021 A | 4/2003 |
| JP | 2004-099366 A | 4/2004 |
| JP | 2005-074253 A | 3/2005 |

OTHER PUBLICATIONS

Makoto Shinohara, "Yuki Hiryo no Yoeki Saibai—Heiko Fukushiki Mukikaho no yoru Yoekinai Biseibutsu Seitaikei Kochikubo", Agriculture and horticulture, vol. 81, No. 7, pp. 753-764 (Jul. 2006).

National Institute of Vegetable and Tea Science, "100% Yuki Hiryo de Yoeki Saibai, Hakko Gijutsu Oyo shi Jitsuyoka Medo", The Chemical Daily, p. 4 (Jan. 27, 2006).

* cited by examiner

METHOD FOR PRODUCING BIOMINERAL-CONTAINING SUBSTANCE AND ORGANIC HYDROPONICS METHOD

This application is the United States national phase application of International Application PCT/JP2006/324146 filed Dec. 4, 2006.

FIELD OF THE INVENTION

The present invention relates to a method for producing a biomineral-containing substance and an organic hydroponics method, particularly to a technique to produce a nutrient solution for plant culture utilizing a biomineral fermentation method to rapidly mineralize organic materials and obtain the biomineral absorbable by plants, as well as a hydroponics method using the nutrient solution obtained by this technique. Note that the biomineral means an inorganic ingredient originated from an organism.

BACKGROUND ART

In recent years, from a standpoint that a recycling society should be constructed, movement to reduce usage of chemical fertilizers and promote usage of organic fertilizers has become active worldwide.

However, in hydroponics which is expanding in production of vegetables such as tomatoes and flowering plants, addition of organic materials to a nutrient solution has not been realized because a direct addition of organic materials to the nutrient solution causes generation of harmful intermediate decomposition products which cause damage to the root of the plants. Therefore, only chemical fertilizers are used for a nutrient solution at present.

On the other hand, various attempts have been made to provide techniques to utilize organic materials even for hydroponics.

For example, a trial has been made to mineralize organic materials prior to utilization for a nutrient solution (Refer to Patent Documents 1 to 3 and Non-patent Document 1). However, decomposition of a nitrogen component did not proceed beyond the production of ammonia by this method, presumably because decomposing a large amount of organic materials at one time in order to increase efficiency all the more generated a large amount of intermediate decomposition products, such as low molecular weight organic compounds and ammonia, resulting in destroying the nitrifying bacteria which decompose ammonia into nitric acid. Therefore, effort to utilize ammonia for a nutrient solution has been made but limited to utilization as a part of the fertilizer, because excess ammonia causes damage to crops.

Consequently, a method to utilize a nitrification reaction tank in order to generate nitric acid, which is more suitable as a fertilizer, from ammonia was developed (Refer to Patent Documents 4 to 7 and Non-patent Document 1). However, this method requires two reaction tanks, i.e., one tank for ammonification in which organic nitrogen is decomposed to ammonium nitrogen and the other tank for nitrification in which ammonium nitrogen is oxidized to generate nitrate nitrogen. Furthermore, it was difficult to stably obtain nitric acid because the nitrification reaction was unstable. In addition, there was a problem of bad smell due to incomplete decomposition in many cases.

In another method, a porous solid medium inhabitable for nitrifying bacteria is utilized to allow direct addition of organic materials into the nutrient solution (Refer to Patent Document 8). However, this was a restrictive technique because it requires utilization of a specific solid medium and cannot apply to other culture technologies, such as rock wool culture and water culture, which are in widespread use at present.

Thus, a technique to directly add organic materials to a nutrient solution applicable to any hydroponics technologies has not been put into practical use yet.

[Patent Document 1] Japanese Unexamined Patent Application Publication No. 2002-137979
[Patent Document 2] Japanese Unexamined Patent Application Publication No. 2001-010885
[Patent Document 3] JP 2000-264765 A
[Patent Document 4] JP 2005-074253 A
[Patent Document 5] JP 2004-099366 A
[Patent Document 6] JP 2003-094021 A
[Patent Document 7] JP H06-178995 A
[Patent Document 8] JP H06-125668 A
[Non-patent Document 1] "Management of Nutrients and solid Media in Drip Fertigation" Hakuyusha, p. 119-155 (2005)

DISCLOSURE OF THE INVENTION

Problems to be Solved by the Invention

The present invention aims at providing a method of biomineral fermentation by which organic materials directly added to water can be smoothly mineralized and a method for producing a nutrient solution for plant culture utilizing the fermentation method. That is, the objective of the present invention is to provide a method to restrain generation of intermediate decomposition products harmful to plant growth and to enable direct addition of organic materials to the nutrient solution by establishing a microbial ecosystem necessary for mineralization of the organic materials in the nutrient solution, thereby stably performing mineralization of the organic materials in a single decomposition tank.

Means to Solve the Problems

As a result of further investigations to overcome the above problems, the present inventors clarified that the decomposition cannot proceed beyond the production of ammonia by the conventional method, because decomposing a large amount of organic materials at one time in order to increase efficiency all the more generated a large amount of intermediate decomposition products, which destroyed the nitrifying bacteria. The present inventors further found that it is possible to maintain the activity of nitrifying bacteria by setting a fermentation period of about two week duration until the microbial ecosystem necessary to decompose organic materials into inorganic nutrients is established in the nutrient solution. In addition, the inventors also found that the microbial ecosystem which smoothly decomposes organic materials into inorganic nutrients can be maintained by adding a small amount of the organic materials to the extent that they do not collapse the microbial ecosystem in the nutrient solution every day during the fermentation period (gradual addition) or by adding an amount of the organic materials to the extent that they do not either collapse the microbial ecosystem at one time at the beginning of fermentation. Furthermore, the inventors found that after the fermentation period is completed, even if a considerable amount of organic materials to the extent necessary for the plant culture is added, it is rapidly decomposed.

Once the fermentation period is completed, it becomes possible to restrain generation of intermediate decomposition products harmful to the microbial ecosystem and plants and to smoothly mineralize a large amount of organic materials. Furthermore, it becomes possible to decompose organic nitrogen to nitric acid with a single decomposition tank. Therefore, an unprecedented revolutionary culture method has been established, by which good growth of plants is enabled without damaging them even if the organic materials are directly added to the nutrient solution for hydroponics and drip fertigation.

The present inventors have completed the present invention based on these findings.

An embodiment of the present invention is a method for producing a biomineral-containing substance, comprising establishing a microbial ecosystem necessary for stable mineralization of organic materials by gradually adding the organic materials to water and fermenting the resulting mixture.

An embodiment of the present invention is a method for producing a biomineral-containing substance, comprising establishing a microbial ecosystem necessary for stable mineralization of organic materials by adding the organic materials to water at one time and fermenting the resulting mixture.

An embodiment of the present invention is a biomineral-containing substance obtained by the methods described in the preceding two paragraphs.

An embodiment of the present invention is a biomineral-containing substance described in the preceding paragraph used for a nutrient solution for plant culture.

An embodiment of the present invention is a method of hydroponic culture of a plant, comprising utilizing the biomineral-containing substance described in the preceding two paragraphs as at least a part of a nutrient solution and culturing the plant while directly adding organic materials to the nutrient solution.

Effect of the Invention

According to the present invention, by gradual addition or one-off addition of organic materials and setting of a fermentation period until the microbial ecosystem in the nutrient solution is established, it is possible to restrain generation of harmful intermediate decomposition products and achieve good growth of the plant. Furthermore, a multiple parallel fermentation by which organic nitrogen can be stably decomposed up to nitric acid with a single decomposition tank can be realized. Therefore, according to the present invention, a method in which the organic materials can be directly added to the nutrient solution is provided in the plant culture technology using a nutrient solution and it becomes possible to produce the nutrient solution for hydroponics or drip fertigation or a liquid fertilizer for additional fertilization from organic materials only.

Furthermore, the present invention not only enables production of the nutrient solution using various raw materials, but also is promising as an effective utilization method of organic waste, because organic materials, whether solid or liquid, can be used to make the nutrient solution.

In addition, the biomineral-containing substance of the present invention can be utilized as a fast-acting fertilizer for additional fertilization besides hydroponics. Although conventionally organic materials utilizable for drip fertigation were limited to liquid, it is possible to produce a nutrient solution using solid organic materials as a raw material according to the present invention.

Furthermore, according to the hydroponic method of the present invention, it is possible to restrain proliferation of wilt disease bacteria, which brings serious damage to solanaceous plants such as tomatoes, and to prevent occurrence of bacterial wilt disease.

BRIEF DESCRIPTION OF THE DRAWINGS

FIG. 1-1 is a graph showing the temporal change of the amount of ammonia and nitric acid generated (mg/L) from various organic materials in Test Example 1.

FIG. 1-2 is a graph showing the temporal change of the amount of nitric acid generated (mg/L) when bean curd refuse and bark compost were added in Test Example 1.

FIG. 11 shows an appearance of a seedling of tomato settled in Example 1.

FIG. 12 shows an appearance of tomatoes grown in Example 1.

DESCRIPTION OF THE PREFERRED EMBODIMENTS

Hereinafter the present invention will be illustrated in detail.

As previously described, in the conventional method, since a large amount of organic materials is added to water at one time, many microorganisms including nitrifying bacteria are destroyed by a large amount of intermediate decomposition products generated during the course of decomposition of the organic materials, resulting in incomplete mineralization of the organic materials, especially organic nitrogen.

On the other hand, in the method for producing the biomineral-containing substance of the present invention, by gradual addition or one-off addition of organic materials into water followed by fermentation, a stable microbial ecosystem is established in water and stable and smooth mineralization (biomineralization) of the organic materials becomes possible. In the stable microbial ecosystem after the fermentation period has been completed, since various microbial species, including nitrifying bacteria, intrinsically existing in water and air coexist while maintaining balance, a considerable amount of the organic materials can be smoothly mineralized even if it is directly added and the microbial ecosystem does not collapse either.

Examples of microorganisms necessary for mineralization of organic nitrogen in organic materials include, but are not limited to, protozoa, bacteria, ammonification microorganisms such as filamentous bacteria, nitrifying bacteria belonging to genus *Nitrosomonas* and genus *Nitrobacter*, and the like.

The organic material used in the present invention may be any material containing organic nitrogen such as protein and its decomposition product, amino acid, and ammonia, whether solid or liquid. Specific examples include organic fertilizers such as corn steep liquor, compost, green manure, fermented fertilizer, and fallen leaves; food residue such as fish flour, oil meal, bean curd refuse, kitchen garbage, and rice bran; organic agricultural waste such as barnyard manure and paddy straw; organic waste such as various sludge; and various waste water containing organic components. Especially preferred are corn steep liquor, oil meal, fish flour, and bean curd refuse, all having a high nitrogen content. The organic materials with any shape may be used as long as they are decomposed by a microorganism. Massive materials may be used after shredding or pulverizing.

The water used in the present invention may be any water in which various microorganisms in the environment can exist. Natural water such as ground water, tap water, seawater, etc. may be used. Especially preferred is ground water.

In the present invention, it is preferable that water is inoculated with a microorganism source besides the aforementioned organic materials to promote establishment of the microbial ecosystem. Examples of the microorganism source include, but are not limited to, soil such as horticultural soil, compost such as bark compost, stone, and sand.

The amount of the microorganism source to be added may be $10^8$ to $10^{13}$ cells/L, preferably $10^{10}$ to $10^{11}$ cells/L. The amount of the soil or bark compost to be added, if used as a microorganism source, is 5 to 50 g/L, preferably 10 to 20 g/L. The microorganism source is preferably added within 10 days after initiation of fermentation, especially preferably at the time point of beginning of fermentation.

According to an embodiment of the present invention, an organic material is added to water gradually in small portions compared to water volume and fermented. The term "add gradually" (gradual addition of) the organic material in the present invention means a split addition in small portions compared to water volume to the extent that the microbial ecosystem in the water does not collapse, not adding a large amount in a lump.

The amount of the organic material which may be added at one time may be determined as needed depending on the decomposability of the organic material, temperature condition, and the like. Specifically the amount of the organic material to be added per 1 L of water is 1 to 30 mg at a time, preferably 3 to 12 mg at a time, as a nitrogen content. The total amount of the organic material to be added is 0.05 to 1 g at a time, preferably 0.1 to 0.4 g at a time, per 1 L of water. When corn steep liquor is used as the organic material, the amount to be added is 0.05 to 1 g at a time, preferably 0.1 to 0.2 g at a time, per 1 L of water. Frequency of addition of the organic material is one time per 1 to 7 days, preferably one time per day.

In addition, when 5 g/L or more of the microorganism source such as soil or bark compost is added to water, the amount of the organic material to be added may be increased to about 2 to 5 times. This is presumably due to the buffering effect by which the soil particles or the like adsorb harmful intermediate decomposition products. For example, if a microorganism source such as soil is not added, the amount of the organic material to be added is 0.05 to 1 g at a time per 1 L, while, when 5 g/L of soil is added, it becomes possible to add up to 2 to 5 g of the organic materials at a time per 1 L.

According to an embodiment of the present invention, the organic material is added to water in a lump at the time of initiation of fermentation.

In the present invention, the amount of the organic material to be added is to the extent that the establishment of the microbial ecosystem in water is not prevented. Therefore, the amount to be added may be determined as needed depending on various conditions including the decomposability of the organic material, temperature condition, and the like. Specifically the amount of the organic material to be added per 1 L of water is 1.5 to 30 mg at a time, preferably 3 to 12 mg at a time, as a nitrogen content. The total amount of the organic material to be added is 0.05 to 1 g, preferably 0.1 to 0.4 g, per 1 L of water. When corn steep liquor is used as an organic material, the amount to be added is 0.05 to 1 g, preferably 0.1 to 0.2 g, per 1 L of water.

In addition, when 5 g/L or more of the microorganism source such as soil or bark compost is added to water, the amount of the organic material to be added may be increased to about 2 to 5 times.

In the present invention, fermentation is continued for the time period necessary until the microbial ecosystem necessary for stable mineralization of the organic material is established in water. Therefore, this fermentation period varies depending on the kind of water and organic material to be used, the amount of the organic material to be added, temperature condition, and the like. A rough target of completion of the fermentation period is the time when the nitric acid generation in water reaches the maximum, which is approximately 7 to 21 days, preferably 2 weeks.

Fermentation conditions during the fermentation period are at ambient temperature, preferably 20 to 32° C., and under an aerobic condition with aeration, shaking, etc.

Note that the fermentation period and fermentation conditions mentioned above are features of embodiments of the present invention.

The fermentation liquor (biomineral-containing substance) obtained after completion of the fermentation period contains abundant biominerals, such as nitrate nitrogen absorbable by plants. In addition, since a microbial ecosystem necessary for stable mineralization of the organic materials has been established in the biomineral-containing substance, the organic materials added can be rapidly mineralized.

Therefore, the biomineral-containing substance obtained by embodiments of the present invention may be used for plant culture. Specific examples of its application include a nutrient solution for hydroponics or drip fertigation or a liquid fertilizer for additional fertilization. It is also possible to dry and solidify the biomineral-containing substance to produce a solid fertilizer.

In addition, the biomineral-containing substance in the present invention includes not only the fermentation liquor itself obtained by fermentation with the aforementioned method, but also the fermentation liquor treated with filtration, centrifugation, etc. and their concentrates obtained by resin adsorption or dialysis, as well as their dry substance.

Next, the hydroponic culture method of the present invention will be illustrated.

The present invention is a hydroponic culture method characterized by that the biomineral-containing substance obtained by the aforementioned method is used as at least a part of the nutrient solution and by that the plant is cultured with direct addition of the organic material to the nutrient solution. Hydroponic culture is a culture method in which nutrient and water necessary for the growth of plant are given as a liquid fertilizer and includes water culture and fog culture not using a medium and solid culture using a medium. The present invention is suitably used for water culture.

A plant cultured in the present invention is not particularly limited as long as the plant is usually cultured by hydroponics. Specific examples include solanaceous plants such as tomato and eggplant, leaf vegetables such as leaf lettuce and lettuce, and flowers and ornamental plants such as rose. Especially preferred are tomato and leaf lettuce.

Examples of the method to produce the nutrient solution using the aforementioned biomineral-containing substance include serving, as a nutrient solution, the fermentation liquor to plant culture, either as it is or after adjusting the component composition by addition of other fertilizer component or by dilution. In addition, it is possible to produce a liquid fertilizer by concentrating the obtained fermentation liquor and to add the liquid fertilizer to the nutrient solution for plant culture prepared beforehand or to water. Furthermore, additives such as antiseptics may be mixed as needed to the nutrient solution for plant culture obtained as mentioned above.

In the present invention, the aforementioned plant culture can be carried out with a similar method to general hydroponics, except that the organic materials are directly added to the above-mentioned nutrient solution. The organic materials mentioned in the present invention is added to supplement the nutrients consumed and any materials may be used as long as they are usable in the aforementioned method for producing biomineral-containing substance. Especially preferred are corn steep liquor, oil meal, fish flour, bean curd refuse, etc. having a high nitrogen content.

Since the nutrient solution used in the present invention can be very smoothly mineralized even if a considerable amount of the organic material is directly added at one time, the amount of the organic material to be added is not particularly limited. Preferably, however, the amount of the organic material to be added at a time per 1 L of the nutrient solution is 30 to 150 mg as a nitrogen content and is 1 to 5 g as the total organic material. When corn steep liquor is used as the organic material, 1 to 5 g is added at a time. Frequency of addition is one time per 1 to 14 days, preferably one time per day.

Culture condition may be selected as needed suitably for the plant cultured. In order to rapidly mineralize the organic material in the nutrient solution, it is preferable to culture at ambient temperature, preferably 20 to 32° C. and in an aerobic condition.

By culturing the plant according to the aforementioned method, the yield is similar to or more than the conventional hydroponics, and the quality is no less than the conventional hydroponics. Furthermore, it was clarified that the occurrence of bacterial wilt disease which brings serious damage to solanaceous plants such as tomatoes can be restrained by the hydroponic culture of the present invention.

Hereinafter the present invention will be specifically illustrated showing the examples, etc.

Test Example 1

Biomineralization of Various Organic Materials

A 500 ml Erlenmeyer flask was charged with 100 ml of distilled water, 1 g of soil, and 1 g of various organic materials and decomposition was carried out at 25° C. The flask was shaken at 120 rpm for aeration. As the organic material, rapeseed oil cake (Miki Co., Ltd.), corn oil meal (Ohta Oil Mill Co., Ltd.), fish flour (Tosho Co., Ltd.), and Corn Steep Liquor (Sakata Seed Co., hereinafter abbreviated as CSL) were used. As the soil, horticultural soil (commercial name: Naeichiban, Zen-Noh (National Federation of Agricultural Cooperative Associations)) was used (same in the following experiments). A similar test was carried out as a control without adding soil.

Figure 11:
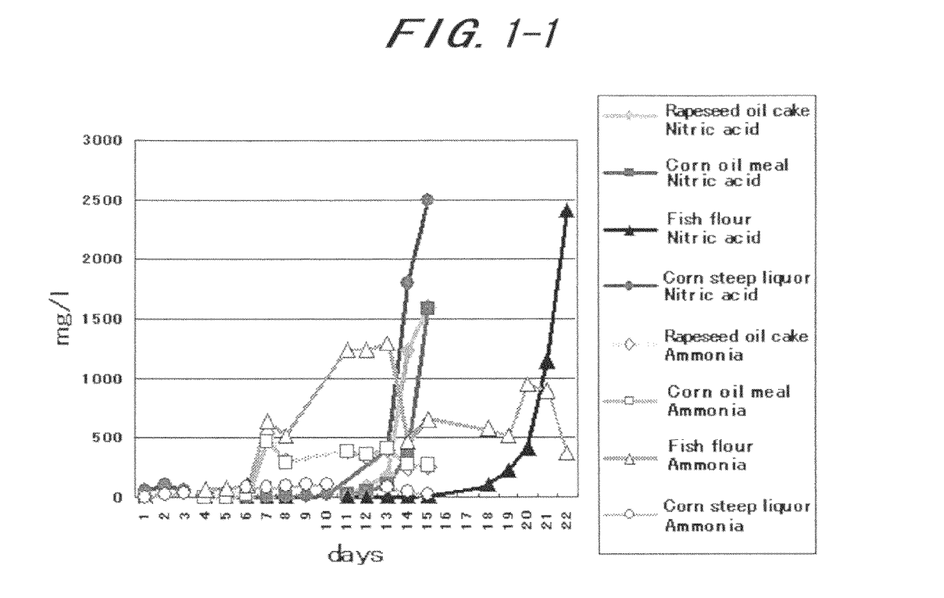

The amount of ammonia and nitric acid generated from various organic materials was measured every day. RQflex (manufactured by Merck KGaA) was used for measurement of both of ammonia and nitric acid. The results are shown in FIG. 1-1.

As a result, plant materials such as rapeseed oil cake, corn oil meal, and corn steep liquor generated the maximum amount of ammonia in about 1 week and all nitrogen contained was mineralized in calculation (FIG. 1-1). Generation of nitric acid reached the maximum after additional 1 week. Fish flour showed a tendency to generate ammonia and nitric acid slightly slowly, i.e., ammonification and nitrification were observed after about 10 days and after about 3 weeks, respectively. Note that in the control area where the soil was not added, although decomposition up to ammonia occurred, nitrification was not observed (results not shown).

Figure 12:
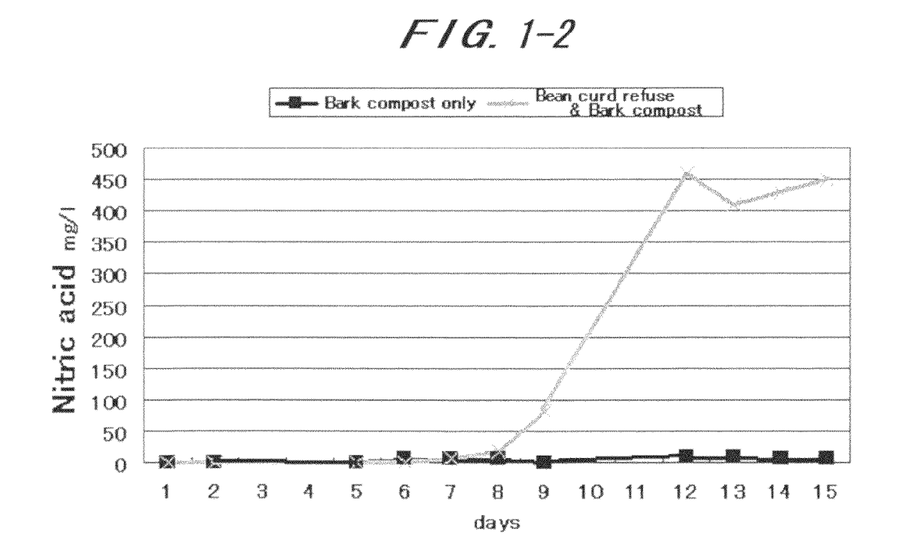

When another test was performed using bark compost (Shimizu Harbor Wood Industry Cooperative Association) instead of soil and using commercial bean curd refuse (u-nohana) as the organic material similarly to the above, nitrification occurred (FIG. 1-2).

Test Example 2

Addition Condition of Microorganism and Organic Materials

A. Influence of Presence or Absence of Addition of Soil

Figure 2:
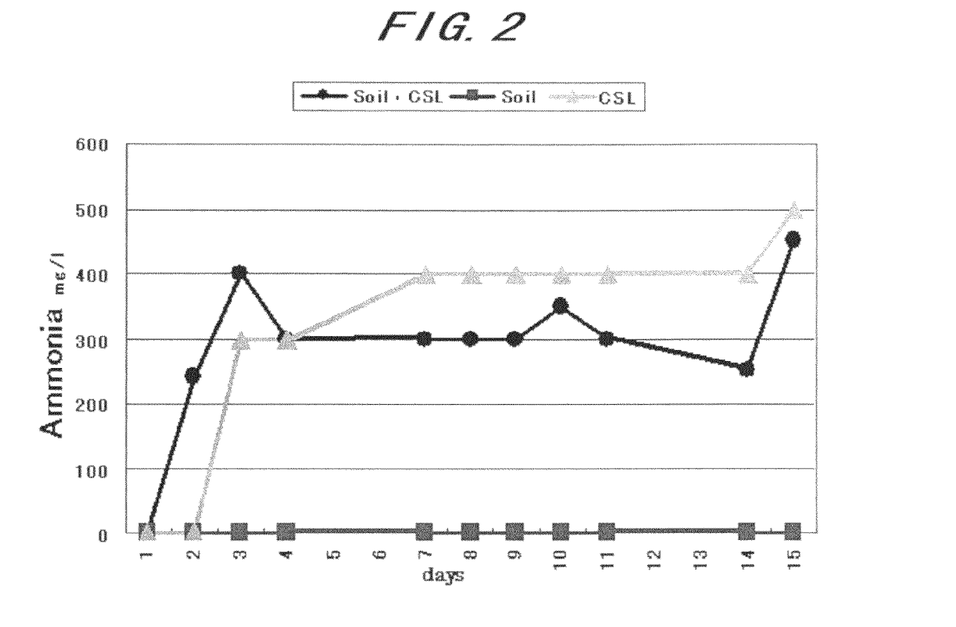
FIG. 2 is a graph showing an effect of the addition of soil on the amount of ammonia generated (mg/L) in Test Example 2A.

A 500 ml Erlenmeyer flask was charged with 100 ml of distilled water, 1 g of CSL and/or 1 g of soil and was shaken (120 rpm) at 25° C. and the amount of ammonia and nitric acid generated was measured every day similarly to Test Example 1. The amount of ammonia and nitric acid generated is shown in FIG. 2 and FIG. 3, respectively.

Figure 3:
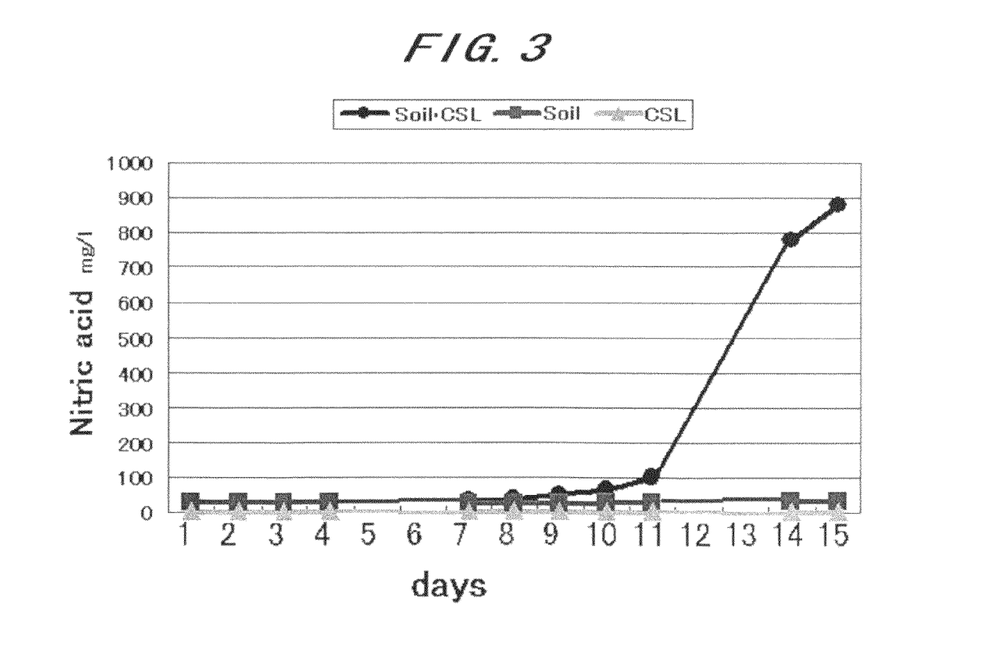
FIG. 3 is a graph showing an effect of the addition of soil on the amount of nitric acid generated (mg/L) in Test Example 2A.

As a result, nitric acid generation was observed only for the experiment with both of soil and CSL added (FIG. 3). Nitric acid generation was not observed with soil or CSL only. Decomposition proceeded up to ammonification with CSL only (FIG. 2).

B. Influence of the Amount of Soil Added

Next, the amount of soil added was changed to examine the influence on the amount of ammonia and nitric acid generated.

Figure 4:
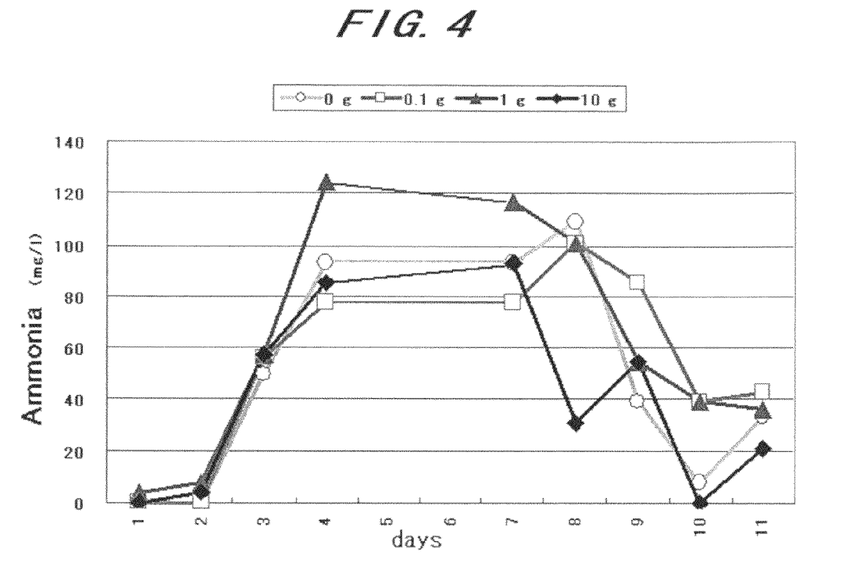
FIG. 4 is a graph showing an effect of the change of the added amount of soil on the amount of ammonia generated (mg/L) in Test Example 2B.
Figure 5:
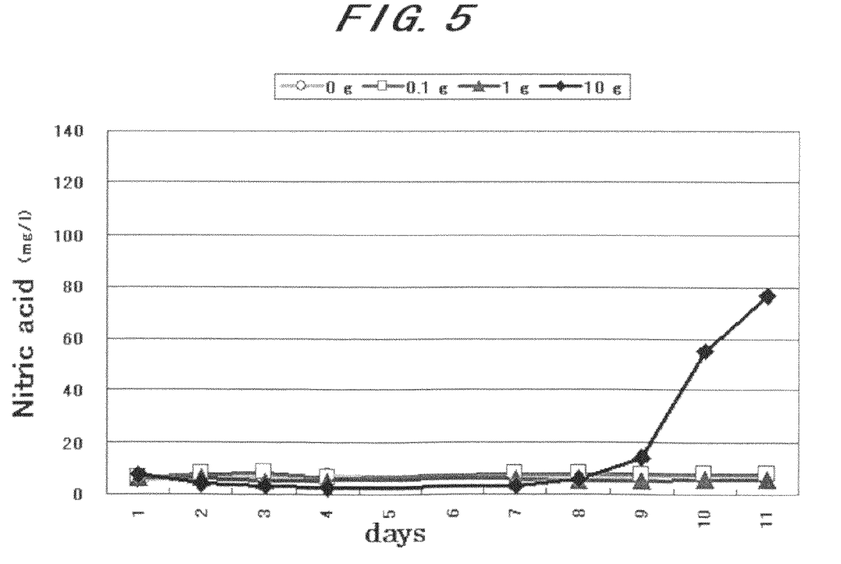
FIG. 5 is a graph showing an effect of the change of the added amount of soil on the amount of nitric acid generated (mg/L) in Test Example 2B.

That is, 5 g of CSL was added to 2 L of water (ground water) followed by adding 0 g, 0.1 g, 1 g, or 10 g of soil, then the mixture was aerated by an air pump at 25° C. The amount of ammonia and nitric acid generated was measured every day similarly to Test Example 1. The amount of ammonia and nitric acid generated is shown in FIG. 4 and FIG. 5, respectively. As a result, nitrification was observed only in the case where 10 g of soil was added (FIG. 5), while in the other cases where less than 10 g of soil was added, decomposition proceeded only up to ammonification (FIG. 4).

C. Nitrification with Gradual Addition and without Soil

The examination was carried out with the gradual addition of small portions compared to water volume every day, not adding a large amount of organic materials at the initial stage of the reaction.

Figure 6:
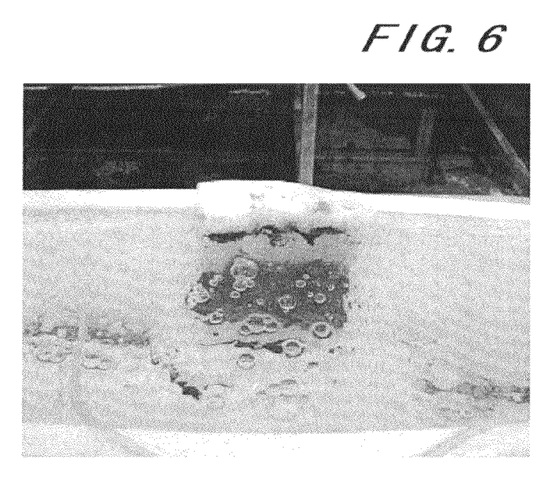
FIG. 6 shows a method of adding soil in Test Example 2C.
Figure 7:
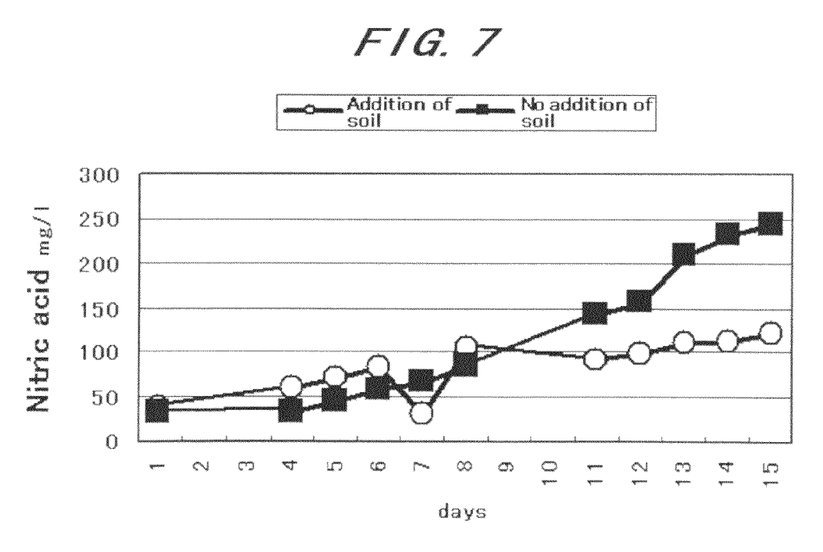
FIG. 7 is a graph showing an effect of the addition of soil on the amount of nitric acid generated (mg/L) in Test Example 2C.

That is, CSL was added at 1 g daily to 15 L of water (ground water) and a "Tokiwa-no-ocha-pack" (Tokiwa's tea pack, Tokiwa Sangyo Co., Ltd.) containing 150 g of soil was suspended like a tea bag (FIG. 6), and the mixture was aerated by an air pump at 25° C. As a control, similar test was done without a bag of soil suspended. The amount of nitric acid generated was measured every day similarly to Test Example 1. The result is shown in FIG. 7. As a result, surprisingly nitrification also proceeded in the control area where soil was not added (FIG. 7).

From this observation, it was considered that, although nitrification does not proceed without addition of soil if a large amount of an organic material (>2.5 g/L) was added at the initial stage as in Experiment B, nitrification may proceed sufficiently with microorganisms living in natural water such as ground water by a method of gradual addition in which the organic material is added in small portions compared to water volume every day as in Experiment C.

D. Influence of the Amount of Soil Added by Means of Gradual Addition

Figure 8:
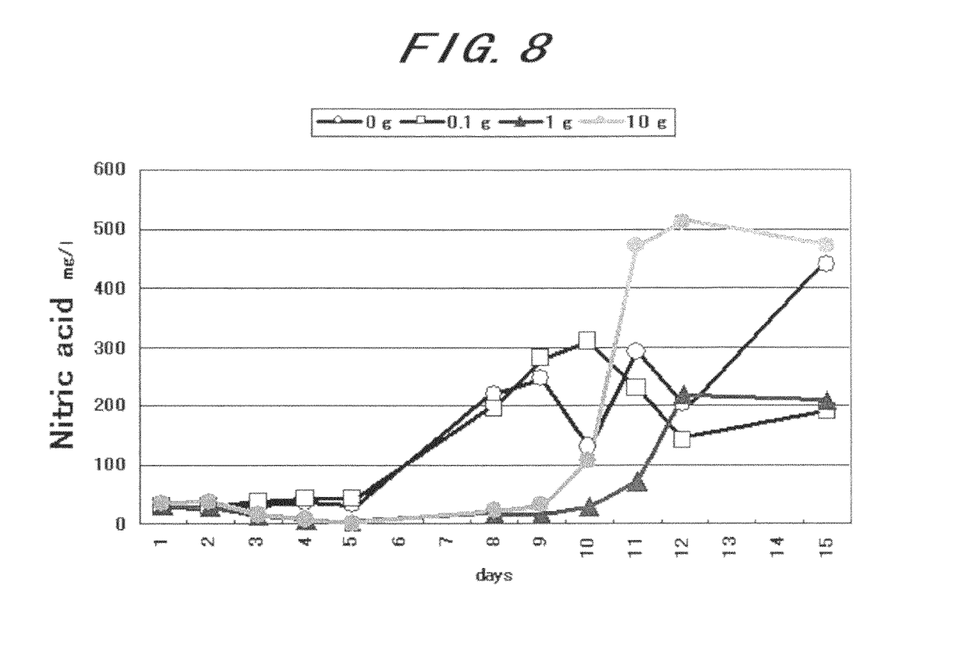
FIG. 8 is a graph showing an effect of the change of the added amount of soil on the amount of nitric acid generated (mg/L) in Test Example 2D.

Therefore, next, 2 L of water (ground water) was added with 0 g, 0.1 g, 1 g, and 10 g of soil and then CSL was added at 1 g daily and the mixture was aerated by an air pump at 25° C. The amount of nitric acid generated was measured every day similarly to Test Example 1. The result is shown in FIG. 8. It was found that nitrification proceeded regardless of presence or absence of the addition of soil by means of gradual addition of the organic material, contrary to the result of Experiment B (FIG. 8).

Figure 9:
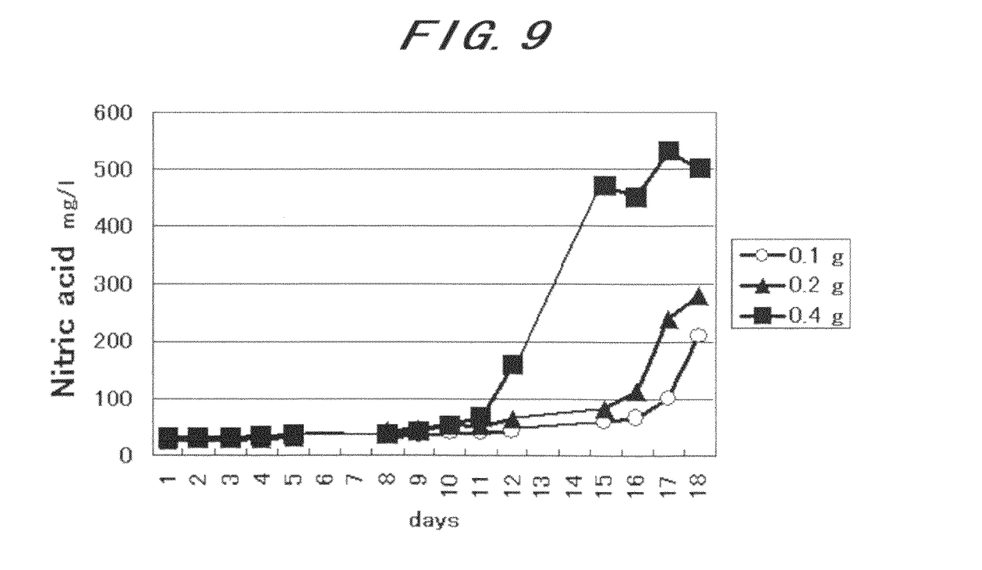
FIG. 9 is a graph showing an effect of the change of the added amount of corn steep liquor on the amount of nitric acid generated (mg/L) in Test Example 2E.

E. Influence of the Amount of Organic Material Added by Means of Gradual Addition CSL was added at 0.1 g, 0.2 g, or 0.4 g daily to 2 L of water (ground water) under aeration with an air pump at 25° C. Soil was not added in each case. The amount of nitric acid generated was measured every day similarly to Test Example 1. The result is shown in FIG. 9. As a result, generation of nitric acid was observed in all test areas (FIG. 9). Therefore, it was found that nitrification proceeds by means of the gradual addition in which the amount of CSL added per day is 1 g/L or less.

DISCUSSION

As stated above, it was found that from the result of Experiment A, that when soil is utilized as a source of microorganisms, nitrification can proceed smoothly even if a large amount of organic materials added (10 g/L or more) at the initial stage.

From the result of the Experiments C, D and E, it was found that nitrification can proceed by gradual addition in which 1 g/L or less (per day) of organic materials is added, even if material rich in microorganisms, such as soil, is not utilized as a source of the microorganisms.

From the result of the Experiment B, it was found that, if 2.5 g per L or more of the organic material is added at the initial stage, nitrification does not proceed unless 5 g/L or more of soil is added, because the nitrifying bacteria are killed. However, it was found that nitrification can proceed by gradual addition of about 0.5 g per L per day as Experiment E, even if soil is not added. It was considered that the nitric acid fermentation was difficult in the conventional mineralization technique because nitrifying bacteria are killed by the addition of a large amount of organic materials at the initial stage.

Example 1

Hydroponic Culture of Tomatoes by Biomineral

First, as a control experiment, the state of the plant was examined in the case where the plant was cultured by hydroponics adding the organic material to the nutrient solution without setting a fermentation period.

That is, a two-week-old seedling of tomato (variety name: "Ponderosa") was settled in a Wagner pot charged with 3 L of water (ground water) and 15 g of CSL was added followed by aeration with an air pump, then the course was observed at ambient temperature. In about 3 days after the initiation of the culture, the plant turned yellow and died. This was presumably because the tomato roots were damaged by the intermediate decomposition products generated by decomposition of the CSL.

Next, after setting a fermentation period during which the organic material in the nutrient solution was mineralized by the method of the present invention, the plant was settled and cultured by hydroponics.

Figure 10A:
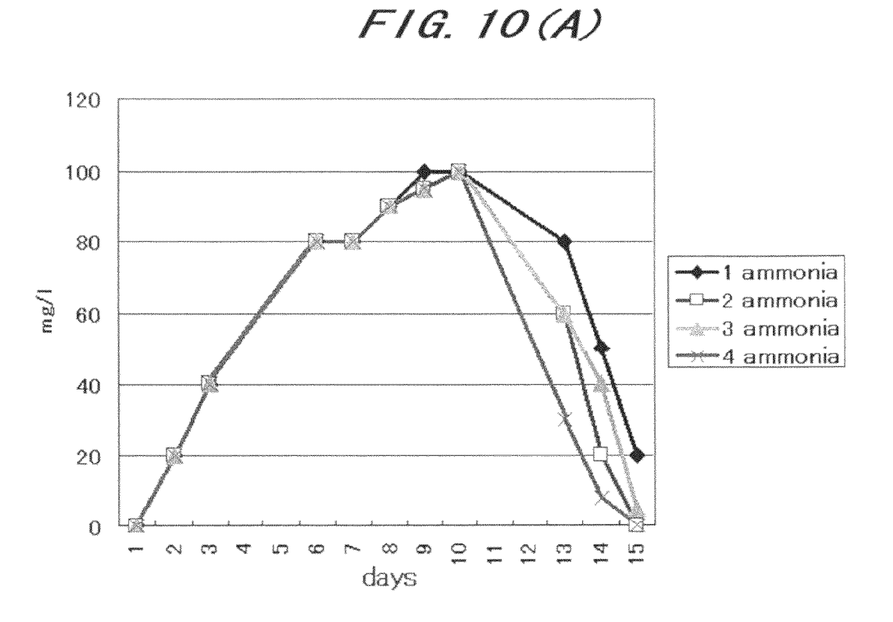
FIG. 10(A) is a graph showing the temporal change of the amount of ammonia generated (mg/L) in Example 1.
Figure 10B:
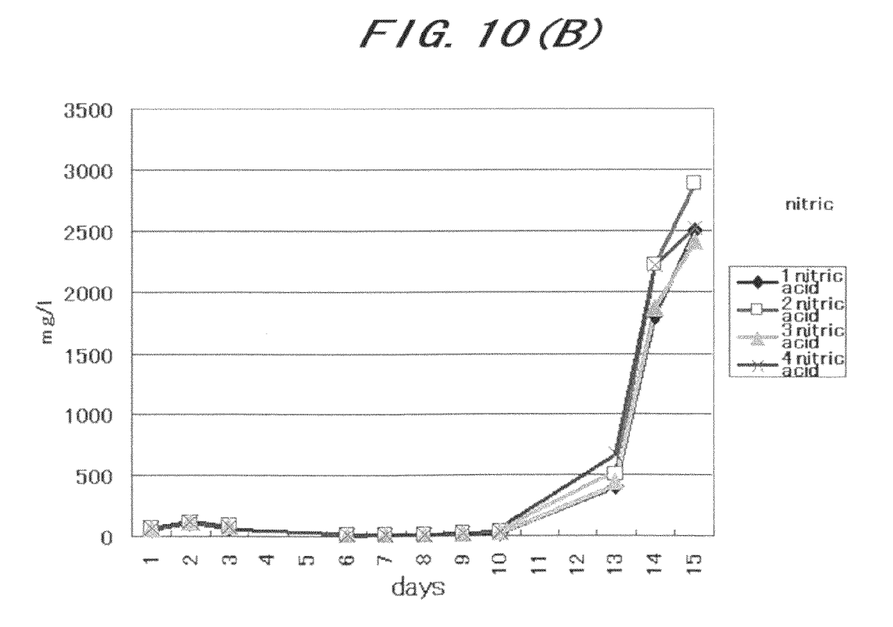
FIG. 10(B) is a graph showing the temporal change of the amount of nitric acid generated (mg/L) in Example 1.

That is, 30 g of soil was added to 4 Wagner pots each charged with 3 L of water (ground water) followed by aeration with an air pump at ambient temperature. Five g of CSL was added to each pot every day. The amount of ammonia and nitric acid generated was measured every day similarly to Test Example 1. The amount of ammonia and nitric acid generated is shown in FIG. 10(A) and FIG. 10(B), respectively. In FIGS. 10(A) and (B), "1 ammonia (nitric acid)" means the amount of ammonia (nitric acid) generated in the pot No. 1. As for the pots No. 2 to 4, the same definition is applied. As a result, nitrification reached the maximum in about 2 weeks for the 4 pots (FIG. 10(B)).

Two weeks after the initiation of addition of CSL, a two-week-old seedling of tomato (variety name: "Ponderosa") was settled one by one per pot (FIG. 11), and hydroponic culture was carried out while continuing aeration at ambient temperature (biomineral area). At the time when the seedling was settled, 30 g of oyster shell lime (commercial name: "Seruka", Zen-Noh) was added to each pot to fill up the deficiency of the inorganic component such as calcium, magnesium, etc. The amount of CSL added after the settlement was 1 to 5 g per pot per day.

On the other hand, as a control, hydroponic culture was carried out similarly to the biomineral area except that a nutrient solution containing a chemical fertilizer (Otsuka A Formulation, Otsuka Chemical Co., Ltd.) mixed with water was used. Additional fertilizer was given every day maintaining the amount of nitrogen to be fertilized equal to that of the biomineral area.

As a result, 4th week after the settlement, satisfactory growth was observed for both of the biomineral area (the left row of FIG. 12) and chemical fertilizer area (the right row of FIG. 12) and there was no difference in the growth of tomatoes. Therefore, it was clarified that the method of the present invention in which the organic material is directly added to the nutrient solution gives the growth equal to that of the conventional method.

Example 2

Hydroponic Culture of Leaf Lettuce by Biomineral

The culture test was carried out also for leaf lettuce.

That is, CSL was added at 1 g daily to a planter (63×23×18 cm) containing 15 L of water (ground water) and a fermentation period in which aeration was continued at ambient temperature was set. Two weeks later, after confirming that the nitrification proceeded as shown in FIG. 7, 16 about one-week-old seedlings of leaf lettuce ("Okayama Leaf Lettuce", Takii & Co., Ltd.) per one planter were settled and the hydroponic culture was started at ambient temperature (biomineral area). CSL was directly added to the nutrient solution after the settlement at the amount of 1 to 3 g per day.

As a chemical fertilizer area (control), hydroponic culture was carried out similarly to the biomineral area except that the nutrient solution containing a chemical fertilizer (Otsuka A Formulation, Otsuka Chemical Co., Ltd.) mixed with water was used. In addition, additional fertilizer was given every day maintaining the amount of nitrogen component to be fertilized equal to that of the biomineral area.

Figure 13:
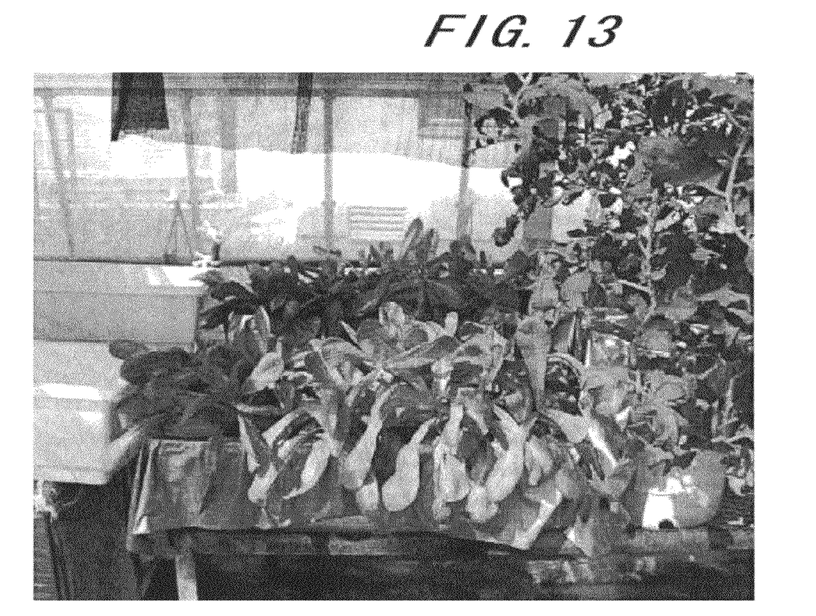
FIG. 13 shows an appearance of leaf lettuce grown in Example 2.

As a result, the yield from the whole planter was compared between the biomineral area (the near side of FIG. 13) and the chemical fertilizer area (the far side of FIG. 13) 4th week after the settlement, and it was 350 g in the biomineral area and 312 g in the chemical fertilizer area, respectively. The growth slightly better was in the biomineral area. No particular difference was observed between the both areas in the color of the leaves and the taste.

Therefore, it was clarified that the method of the present invention in which the organic material is directly added to the nutrient solution gives the growth equal to or better than the conventional method for leaf lettuce. Consequently, it is assumed that other plants may also be cultured by the method of the present invention.

Test Example 3

Test of Bacterial Wilt Disease Resistance by Biomineral Culture

The bacterial wilt disease resistance of the plants cultured by the method of the present invention was tested as follows.

First, wilt disease bacteria (*Ralstonia solanacearum* 03-01487 strain) were statically cultured on the CPG agar medium (composition: 1 g of casamino acid, 10 g of peptone, 5 g of glucose, and 16 g of agar per L) at 32° C. for 3 days. The proliferated bacteria biomass was suspended in sterilized water to make a source of wilt disease bacteria inoculation.

Then, CSL was added at 1 g daily to a planter (63×23×18 cm) containing 15 L of water (ground water) and a fermentation period was set in which aeration was continued at ambient temperature. Two weeks later, 16 two-week-old seedlings of tomato (variety name: "Ponderosa") per one planter were settled and the hydroponic culture was started at 32° C. (biomineral area). One gram per day of CSL was added after the settlement. The nutrient solutions were inoculated with the wilt disease bacteria obtained as mentioned above ($10^8$ to $10^{10}$ cells) at 2, 9 and 11 days after the settlement.

On the other hand, as a chemical fertilizer area (control), hydroponic culture and inoculation were carried out similarly to the biomineral area except that the nutrient solution containing a chemical fertilizer (Otsuka A Formulation, Otsuka Chemical Co., Ltd.) mixed with water was used. In addition, additional fertilizer was given every day maintaining the amount of nitrogen component to be fertilized equal to that of the biomineral area.

Figure 14:
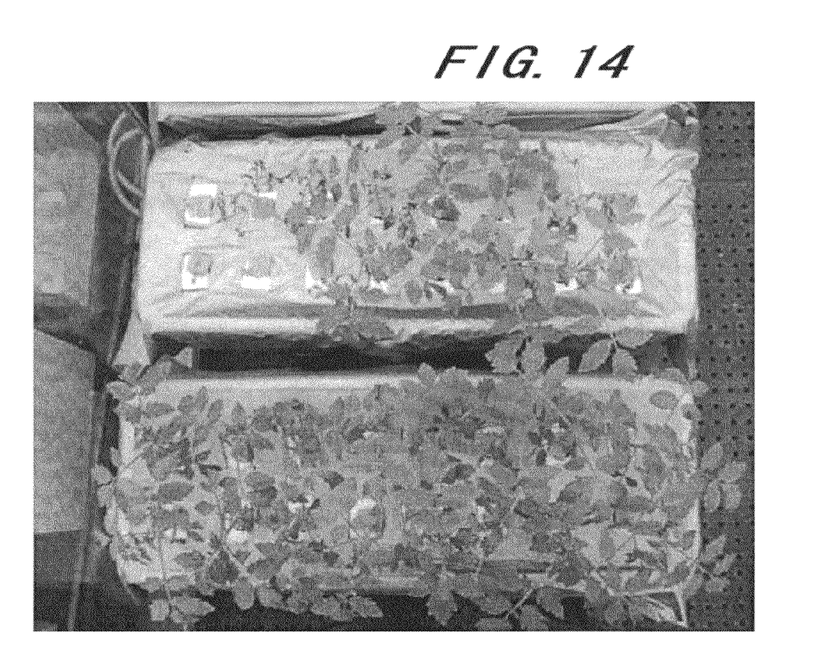
FIG. 14 shows an appearance of tomatoes inoculated with wilt disease bacteria in Test Example 3.

As a result, 11 seedlings wilted by bacterial wilt disease in the chemical fertilizer area on the 13th day after the settlement (the upper side of FIG. 14), while no disease occurred at all in the biomineral area (the lower side of FIG. 14).

Consequently, it was clarified that the occurrence of bacterial wilt disease can be restrained by culturing according to the method of the present invention.

INDUSTRIAL APPLICABILITY

According to the present invention, the hydroponic culture method in which organic materials can be directly added to a nutrient solution is provided and it becomes possible to produce the nutrient solution for hydroponic culture and drip fertigation or the liquid fertilizer for additional fertilization from the organic materials only. Although conventionally the organic material utilizable for drip fertigation was limited to liquid, production of the nutrient solution from a solid organic material as a raw material has become possible by the present invention.

Furthermore, the present invention not only enables production of the nutrient solution using various raw materials, but also is promising as an effective utilization method of organic waste, because organic materials, whether solid or liquid, can be used to make the nutrient solution.

In addition, according to the hydroponic culture of the present invention, the occurrence of bacterial wilt disease which causes serious damage to the solanaceous plants such as tomatoes can be prevented.

The invention claimed is:

1. A method for producing a biomineral-containing nutrient solution comprising:
   (a) gradually adding an organic material to water, said organic material being selected from the group consisting of corn steep liquor, compost, green manure, fermented fertilizer, fallen leaves, fish flour, oil meal, bean curd refuse, kitchen garbage, rice bran, barnyard manure and paddy straw, said organic material being added in an amount of 0.05 to 1 g per 1 L of water one time per 1 to 7 days,
   (b) fermenting the resulting mixture under aeration, such as to establish a microbial ecosystem, and (c) decomposing organic nitrogen in the organic material to nitric acid.

2. The method of claim 1, wherein after said microbial ecosystem is established, the method further comprising a step (d) of adding said organic material in an amount of 1 to 5 g per 1 L of water one time per 1 to 14 days and a step (e) of nitrifying organic nitrogen in said organic material by said microbial ecosystem to thereby obtain a nutrient solution containing nitrate nitrogen derived from said organic material.

3. The method of claim 1, wherein said organic material is a solid or a liquid containing organic nitrogen.

4. The method of claim 2, wherein said organic material is a solid or a liquid containing organic nitrogen.

5. The method of claim 1, wherein said organic material is selected from the group consisting of corn steep liquor, oil meal, fish flour, rice bran, barnyard manure and bean curd refuse.

6. The method of claim 2, wherein said organic material is selected from the group consisting of corn steep liquor, oil meal, fish flour, rice bran, barnyard manure and bean curd refuse.

7. The method of claim 1, which further comprises adding a microorganism source during step (a).

8. The method of claim 2, which further comprises adding a microorganism source during step (a).

9. The method of claim 7, wherein the microorganism source is selected from the group consisting of soil, compost, stone and sand.

10. The method of claim 8, wherein the microorganism source is selected from the group consisting of soil, compost, stone and sand.

11. The method of claim 7, wherein 5 g/L or more of the microorganism source is added to water and the amount of said organic material to be added is increased to about 2 to 5 times.

12. The method of claim 8, wherein 5 g/L or more of the microorganism source is added to water and the amount of said organic material to be added is increased to about 2 to 5 times.

13. The method of claim 1, wherein fermentation is completed at the time when nitric acid generation in water reaches a maximum.

14. The method of claim 2, wherein fermentation is completed at the time when nitric acid generation in water reaches a maximum.

15. The method of claim 13, wherein fermentation is continued for 7 to 21 days at a water temperature of 20 to 32° C.

16. The method of claim 14, wherein fermentation is continued for 7 to 21 days at a water temperature of 20 to 32° C.

* * * * *